(12) United States Patent
Coffindaffer et al.

(10) Patent No.: US 9,237,995 B2
(45) Date of Patent: Jan. 19, 2016

(54) METHODS OF CLEANSING SKIN AND RINSE-OFF OR WIPE-OFF COMPOSITIONS THEREFOR

(71) Applicant: The Proctor & Gamble Company, Cincinnati, OH (US)

(72) Inventors: Timothy Woodrow Coffindaffer, Maineville, OH (US); Mannie Lee Clapp, Mason, OH (US); Dennis Eugene Kuhlman, Middletown, OH (US); Kenneth Eugene Kyte, III, Lebanon, OH (US); Daniel Burton Sears, Hamilton, OH (US); Barbara Kay Williams, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/027,798

(22) Filed: Sep. 16, 2013

(65) Prior Publication Data

US 2014/0018276 A1 Jan. 16, 2014

Related U.S. Application Data

(63) Continuation of application No. 11/367,815, filed on Mar. 3, 2006, now Pat. No. 8,563,491.

(60) Provisional application No. 60/700,960, filed on Jul. 20, 2005, provisional application No. 60/658,687, filed on Mar. 4, 2005.

(51) Int. Cl.
| | |
|---|---|
| *A61K 8/00* | (2006.01) |
| *A61K 8/37* | (2006.01) |
| *A61K 8/31* | (2006.01) |
| *A61K 8/41* | (2006.01) |
| *A61K 8/92* | (2006.01) |
| *A61Q 1/14* | (2006.01) |
| *A61Q 5/02* | (2006.01) |
| *A61Q 19/10* | (2006.01) |

(52) U.S. Cl.
CPC ... *A61K 8/37* (2013.01); *A61K 8/31* (2013.01); *A61K 8/375* (2013.01); *A61K 8/416* (2013.01); *A61K 8/92* (2013.01); *A61K 8/922* (2013.01); *A61Q 1/14* (2013.01); *A61Q 5/02* (2013.01); *A61Q 19/10* (2013.01)

(58) Field of Classification Search
CPC ............ A61K 8/37; A61K 8/416; A61K 8/92
USPC .......................................... 424/401; 510/130
See application file for complete search history.

(56) References Cited

U.S. PATENT DOCUMENTS

| | | |
|---|---|---|
| 3,761,418 A | 9/1973 | Parran, Jr. |
| 4,389,418 A | 6/1983 | Burton |
| 4,495,079 A | 1/1985 | Good |
| 4,715,982 A | 12/1987 | Zabotto |
| 4,956,170 A | 9/1990 | Lee |
| 5,011,681 A | 4/1991 | Ciotti et al. |
| 5,013,763 A | 5/1991 | Tubsing |
| 5,573,759 A | 11/1996 | Blank |
| 5,585,104 A * | 12/1996 | Ha et al. .................. 424/401 |
| 5,595,984 A | 1/1997 | Blank |
| 5,605,894 A | 2/1997 | Blank |
| 5,607,980 A | 3/1997 | McAtee |
| 5,629,301 A | 5/1997 | Blank |
| 5,652,230 A | 7/1997 | Blank |
| 5,661,119 A | 8/1997 | Hersh et al. |
| 5,665,364 A | 9/1997 | McAtee |
| 5,665,687 A | 9/1997 | Khayat et al. |
| 5,674,511 A | 10/1997 | Kacher et al. |
| 5,741,766 A | 4/1998 | Marion |
| 5,759,557 A | 6/1998 | Epstein |
| 5,776,917 A | 7/1998 | Blank |
| 5,780,458 A | 7/1998 | Blank |
| 5,811,111 A | 9/1998 | McAtee |
| 5,869,071 A | 2/1999 | Wieselman |
| 5,989,536 A | 11/1999 | Deckner |
| 6,023,464 A | 2/2000 | Woundy |
| 6,080,708 A | 6/2000 | Glenn et al. |
| 6,112,305 A | 8/2000 | Dancs et al. |
| 6,115,136 A | 9/2000 | Krishnan |
| 6,182,136 B1 | 1/2001 | Ramanathan et al. |

(Continued)

FOREIGN PATENT DOCUMENTS

| | | |
|---|---|---|
| DE | 150759 A1 | 9/1981 |
| DE | 102004045253 A1 | 4/2006 |

(Continued)

OTHER PUBLICATIONS

Flick, E., Cosmetic and Toiletry Formulations, 1992, Noyes Publications, 2nd ed., vol. 2, p. 47.*
Flick, E., Cosmetic Additives, 1991, Noyes Publications, pp. 176, 205 & 210.*
Viscosity Tables, V&P Scientific, Inc., Aug. 9, 2010 printed from internet.
International Search Report, PCT/US2006/008006, dated Sep. 12, 2006 (12 pages).
Flick, E., Cosmetics Additives: An Industrial Guide, 1991, Noyes Publications, pp. 742-743.
Poucher's Perfumes, Cosmetics and Soaps, 2000 (Hilda Butler, 10th ed.).

*Primary Examiner* — Gina Justice

(57) ABSTRACT

Methods of cleansing skin comprise the steps of contacting the skin with a cleansing compositions comprising a fatty ester in combination with a lipid, and either rinsing the composition from the skin with water or wiping the composition from the skin with a dry or damp substrate. The cleansing compositions can comprise at least 8%, by weight of the composition, of fatty ester and/or further comprise a nonionic surfactant and less than about 50%, by weight of the composition, of an alcohol solvent such as ethanol, isopropanol, or mixtures thereof. The methods and compositions provide skin cleansing and hydration benefits.

8 Claims, No Drawings

(56) References Cited

U.S. PATENT DOCUMENTS

| | | |
|---|---|---|
| 6,183,766 B1 | 2/2001 | Sine |
| 6,264,963 B1 | 7/2001 | Leifheit |
| 6,342,469 B1 | 1/2002 | Lorant |
| 6,423,329 B1 | 7/2002 | Sine |
| 6,603,758 B1 | 8/2003 | Schmuelling et al. |
| 6,645,511 B2 | 11/2003 | Aronson et al. |
| 6,711,162 B1 | 3/2004 | Ortega et al. |
| 6,716,440 B2 | 4/2004 | Aronson et al. |
| 6,759,376 B2 | 7/2004 | Zhang et al. |
| 6,827,795 B1 | 12/2004 | Kasturi et al. |
| 6,878,380 B2 | 4/2005 | Farrell |
| 6,891,825 B1 | 5/2005 | O'Dell et al. |
| 6,928,463 B2 | 8/2005 | Tene et al. |
| 7,117,526 B1 | 10/2006 | Short |
| 2001/0030977 A1 | 10/2001 | May |
| 2001/0049720 A1 | 12/2001 | Eyer |
| 2002/0004935 A1 | 1/2002 | Huotari et al. |
| 2003/0028650 A1 | 2/2003 | Chen et al. |
| 2003/0095944 A1 | 5/2003 | Midha |
| 2003/0152540 A1 | 8/2003 | Putman et al. |
| 2003/0200321 A1 | 10/2003 | Chen et al. |
| 2004/0005285 A1 | 1/2004 | Midha |
| 2004/0042992 A1 | 3/2004 | Romaine |
| 2004/0081679 A1 | 4/2004 | Simon et al. |
| 2004/0223992 A1 | 11/2004 | Clapp |
| 2006/0239953 A1 | 10/2006 | Clapp et al. |
| 2006/0251606 A1 | 11/2006 | Coffindaffer et al. |

FOREIGN PATENT DOCUMENTS

| | | |
|---|---|---|
| EP | 354331 A1 | 2/1990 |
| FR | 2843540 A1 | 2/2004 |
| FR | 2843541 A1 | 2/2004 |
| FR | 2863873 A1 | 6/2005 |
| GB | 1501942 | 2/1978 |
| JP | 62010009 A | 1/1987 |
| JP | 08092031 A | 4/1996 |
| JP | 11043698 A | 2/1999 |
| JP | 2003201215 A | 7/2003 |
| JP | 2004010553 A | 1/2004 |
| JP | 2004331544 A | 11/2004 |
| JP | 2006056856 A | 3/2006 |
| WO | 90/00189 A1 | 1/1990 |
| WO | 95/26710 A1 | 10/1995 |
| WO | 2004/065536 A1 | 8/2004 |
| WO | 2006/021350 A1 | 3/2006 |

* cited by examiner

METHODS OF CLEANSING SKIN AND RINSE-OFF OR WIPE-OFF COMPOSITIONS THEREFOR

FIELD OF THE INVENTION

The present invention relates to methods of cleansing skin and cleansing compositions comprising a fatty ester in combination with a lipid. The compositions and methods provide skin cleansing and hydration benefits.

BACKGROUND OF THE INVENTION

Personal cleansing products, especially products for cleansing facial skin, are very popular consumer products in today's market. There are several cleansing benefits that such facial cleansing products attempt to achieve, such as removing makeup, removing dead skin, unclogging pores, sebum removal, and the like. While many facial cleansing products are effective in providing these cleansing benefits, many products can irritate the skin or cause the skin to lose moisture and become dried out. Even water alone, when used to cleanse the skin, can cause the skin to lose moisture.

As a result, many consumers resort to using both a facial cleansing product, for achieving cleansing benefits, followed by a skin lotion product to provide hydration benefits to the skin and prevent the skin from drying out.

There thus remains a desire to develop skin cleansing compositions, especially for facial cleansing, that provide effective skin cleansing while improving skin hydration, provide a rich creamy lather, and are easily rinsed from the skin with water or wiped from the skin with a dry or damp substrate.

SUMMARY OF THE INVENTION

The present invention relates to compositions and methods for cleansing skin which also provide skin hydration benefits. The compositions generally comprise a fatty ester in combination with a lipid to provide both cleansing and hydration benefits in a rinse-off or wipe-off cleansing composition. The methods of the present invention generally encompass contacting the skin with a composition of the present invention and either rinsing the composition from the skin with water or wiping the composition from the skin with a dry or damp substrate.

In one embodiment, the present compositions comprise at least 8%, by weight of the composition, of fatty ester to provide skin cleansing and hydration benefits, especially for removing greasy soils from skin (e.g. makeup) in the context of a rinse-off or wipe-off composition.

In one embodiment, the present compositions comprise a nonionic surfactant to allow the compositions to be easily rinsed or otherwise removed from the skin. The nonionic surfactant will preferably have an average HLB of from about 8 to about 20. These compositions tend to be highly aqueous and will comprise a level of alcohol solvent, such as ethanol, isopropanol, or mixtures thereof, of less than about 50%, by weight of the composition.

In one embodiment, the present compositions further comprise a hydrophobic structuring agent. The hydrophobic structuring agent can facilitate the formation of a gel network in the present compositions, which tends to provide a rich, creamy feel on the skin and allows for good application of the product without causing damage to the skin.

DETAILED DESCRIPTION OF THE INVENTION

The present invention relates to methods of cleansing skin and cleansing compositions comprising a fatty ester in combination with a lipid, preferably a high modulus lipid. The compositions can further comprise a number of optional ingredients, such as hydrophobic structuring agents, cationic surfactants, nonionic surfactants, amphoteric surfactants, anionic surfactants, humectants, exfoliating agents, polymeric thickeners, silicones, silicone elastomers, aqueous carrier, and other optional ingredients, and mixtures thereof.

Fatty Esters

Fatty esters are incorporated in the present compositions to provide skin cleansing and skin hydration benefits. Fatty esters can also serve to enhance the spreadability of the lipid and to reduce the tack typically associated with lipids. The fatty esters can be premixed with the lipids, or they can be added separately while the product is warm, or when the product is cooling.

The present compositions will typically comprise fatty esters at a level of at least about 1%, preferably at least about 5%, and more preferably at least about 8%, by weight of the composition. The level of fatty ester in the present composition is preferably no greater than about 40%, preferably no greater than about 30%, and more preferably no greater than about 20%, by weight of the composition. In one embodiment, the present compositions comprise greater than 8%, and preferably greater than about 10%, by weight of the composition, of fatty ester.

The fatty esters of the present invention can include linear and branched fatty ester oils that comprise one or two ester group in the molecule. One type of common fatty ester oil useful in the present invention are the fatty acid mono and polyesters such as cetyl octanoate, octyl isonanoanate, myristyl lactate, cetyl lactate, isopropyl myristate, myristyl myristate, diisopropyl sebacate, isopropyl isostearate, isostearyl isostearate, propylene glycol dipelargonate, 2-ethylhexyl isononoate, 2-ethylhexyl stearate, isopropyl lanolate, 2-ethylhexyl salicylate, diisotearyl malate, isostearyl neopentanoate, isopropyl palmitate, isopropyl adipate, butyl stearate, ethylhexyl isononanoate, decyl oleate, cholesterol isostearate, glycerol monostearate, glycerol distearate, glycerol tristearate, alkyl lactate, alkyl citrate and alkyl tartrate; sorbitol ester, and the like. Preferred fatty esters are isopropyl palmitate and/or isopropyl isostearate.

The esters will preferably have a viscosity below about 100 milliPascals ("mPas"), even more preferably below about 75 mPas, even more preferably below about 50 mPas, and most preferably below about 40 mPas.

The individual fatty groups of the esters will preferably comprise no more than about 22 carbon atoms, more preferably no more than about 18 carbon atoms, and more preferably no more than about 16 carbon atoms. For a single alkyl group having greater than 17 carbon atoms, branched or unsaturated alkyl chains are preferred. Preferably, the total number of carbon atoms in the fatty ester will be less than about 30, even more preferably less than about 25, even more preferably less than about 23.

Lipids

The present compositions will further comprise a lipid to provide skin hydration benefits. Suitable lipids include oils and high modulus lipids. The high modulus lipids of the present invention typically comprise an oil and an oil structurant. Compositions having enhanced skin cleansing and skin hydration benefits can be achieved by combining the lipid with the fatty ester of the present invention. As noted previously, the lipids can be premixed with the fatty esters during the process of making the present compositions.

Lipids are typically incorporated in the present compositions at levels of from about 0.1% to about 20%, preferably from about 0.5% to about 15%, and more preferably from about 1% to about 10%, by weight of the composition. Preferably, the ratio of lipid to fatty ester will typically be no more than about 20:1, more preferably no more than about 10:1, more preferably no more than about 5:1, and more preferably no more than about 2:1. Preferably, the ratio of lipid to fatty ester will typically be at least about 1:15, even more preferably at least about 1:10, even more preferably at least about 1:8, even more preferably at least about 1:4.

A variety of oils are suitable for incorporation as a lipid in the compositions herein. One class of oils useful herein are triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed. Modified triglycerides include materials such as ethoxylated and maleated triglyceride derivatives provided they are liquids. Proprietary ester blends such as those sold by Finetex as FINSOLV® are also suitable, as is ethylhexanoic acid glyceride.

Another type of oil is liquid polyester formed from the reaction of a dicarboxylic acid and a diol. Examples of polyesters suitable for the present invention are the polyesters marketed by ExxonMobil under the trade name PURESYN® ESTER.

A second class of oils suitable for the present invention is liquid and semi-solid hydrocarbons. These include linear and branched oils such as liquid paraffin, squalene, squalane, mineral oil, low viscosity synthetic hydrocarbons such as polyalphaolefin sold by ExxonMobil under the trade name of PURESYN® PAO and polybutene under the trade name PANALANE® or INDOPOL®. Light (low viscosity) highly branched hydrocarbon oils are also suitable.

The lipid of the present invention can be a high modulus lipid that comprises an oil, such as those described previously, and an oil structurant. A variety of oil structurants are suitable for incorporation in the high modulus lipid of the present invention. The oil structurant can be either an organic or inorganic structurant. Examples of organic oil structurants suitable for the invention can be selected from the group consisting of natural or modified fats, fatty acid, fatty amine, natural and synthetic waxes, block copolymers, and mixtures thereof. Suitable block polymers for this application can be those sold under the name KRATON® by Shell. Inorganic structuring agents can be selected from the group consisting of hydrophobically modified silica, hydrophobically modified clay and mixtures thereof. Non-limiting examples of inorganic structurants are BENTONE® 27V, BENTONE® 38V or BENTONE® GEL MIO V from Rheox; and CAB-O-SIL® TS720 or CAB-O-SIL® M5 from Cabot Corporation.

The structurant may be a natural or synthetic crystalline wax. Mineral, animal or plant (vegetable) waxes are all described as natural waxes. Synthetic waxes are described as those waxes that have been synthetically polymerized from raw materials or chemically modified natural waxes.

Among the natural crystalline waxes which may be used are petroleum-based waxes such as paraffin wax and microcrystalline wax. Molecular weights of paraffin waxes generally range from about 360 to about 420 (about 26 to about 30 carbon atoms), although versions with longer chains (molecular weights up to about 600) are available. Typical melting points are from about 126° F. to about 134° F. (from about 52° C. to about 57° C.), with the high molecular weight versions having melting points near about 170° F. (about 77° C.). Paraffin waxes are brittle and the addition of oil tends to weaken the structure (lowers the tensile strength). Microcrystalline wax melting points are from about 145° F. to about 195° F. (from about 63° C. to about 91° C.). The crystals of microcrystalline wax tend to be small and irregular and consist of several types: plates, malcrystalline and needle.

Other suitable oil structurants include animal-derived or plant-derived waxes. Animal waxes can be obtained from such things as bees, insects or whales. These waxes include but are not limited to beeswax, Chinese wax, shellac wax, spermaceti and wool wax. Plant waxes can be derived from beans, leaves and berries. Plant or vegetable waxes can include bayberry, candelilla, carnauba, cotton, esparto, fir, Japan, ouricury, palm, rice-oil, sugar cane, ucuhuba and cocoa butter.

Among synthetic crystalline waxes which may be used are crystalline polymers such as polyethylene, Fischer-Tropsch waxes such as polymethylene, chemically modified waxes, polymerized alpha olefins and synthetic animal waxes. For example, siliconyl beeswax may be used which is beeswax that has been chemically modified.

In addition, the oil structurant may be a natural or synthetic hydrogenated oil. Hydrogenated oils can be hydrogenated vegetable oils, hydrogenated coconut oil, hydrogenated palm kernel oil, hydrogenated rapeseed oil, castorwax and many others.

Petrolatum is a unique hydrocarbon material, as it typically comprises both an oil (e.g. mineral oil) and an oil structurant (e.g. paraffin wax and/or microcrystalline wax). Therefore, petrolatum itself constitutes a high modulus lipid according to the present invention and is a preferred high modulus lipid of the present invention. Petrolatum can also be blended with other lipids of the present invention. Its semi-solid nature can be controlled both in production and by the formulator through blending with other lipids.

The high modulus lipids of the present invention will typically have a Lipid Modulus Value of at least about 50, preferably at least about 100, more preferably at least about 125, and more preferably at least about 150. The Lipid Modulus Value of a lipid material is measured according to the Lipid Modulus Test Method described herein.

Aqueous Phase Hydrophobic Structuring Agents

The present invention optionally comprises no more than about 20%, preferably no more than about 10%, and more preferably no more than about 7.5%, by weight of the composition, of an aqueous phase hydrophobic structuring agent, preferably selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 40° C. The present invention optionally, but preferably, comprises at least 0.5%, more preferably at least 1%, and even more preferably at least 2%, by weight of the composition, of an aqueous phase hydrophobic structuring agent, preferably selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 40° C. These structuring agents can be useful to assist in the formation of the rheological characteristic of the composition which can contribute to the stability of the composition of the present invention. In particular, the aqueous phase hydrophobic structuring agents tend to assist in the formation of the liquid crystalline gel network structures in the present compositions. Indeed, the present compositions preferably comprise a gel network. The "gel network" of the present invention typically comprises an aqueous phase hydrophobic structuring agent and a surfactant. A gel network in the present compositions tends to provide a rich creamy feel and to allow good application of the product without causing damage to the skin.

Suitable hydrophobic structuring agents of the present invention are selected from the group consisting of stearyl alcohol, cetyl alcohol, cetearyl alcohol, myristyl alcohol, arachidic alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, emulsifying waxes (e.g. POLAWAX® NF available from Croda), and mixtures thereof. Preferred structuring agents are selected from the group consisting of stearyl alcohol, cetyl alcohol, behenyl alcohol, steareth-2, and mixtures thereof. Such hydrophobic structuring agents can be provided as mixtures with other hydrophobic structuring agents and/or surfactants.

Cationic Surfactants

The compositions of the present invention can optionally comprise from about 0.1% to about 15%, more preferably from about 0.2% to about 10%, and most preferably from about 0.5% to about 5%, by weight of the composition, of cationic surfactant. Cationic surfactants can be useful in the present compositions to help form a gel network in the present compositions, although formation of a gel network does not require a cationic surfactant.

Non-limiting examples of cationic surfactants useful herein include cationic ammonium salts such as those having the formula:

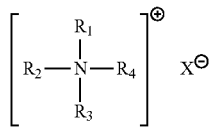

wherein $R_1$, is selected from an alkyl group having from about 12 to about 22 carbon atoms, or from aryl or alkaryl groups having from about 12 to about 22 carbon atoms; $R_2$, $R_3$, and $R_4$ are independently selected from hydrogen, an alkyl group having from about 1 to about 22 carbon atoms, or aromatic, aryl or alkaryl groups having from about 6 to about 22 carbon atoms; and X is an anion selected from chloride, bromide, iodide, acetate, phosphate, nitrate, sulfate, methyl sulfate, ethyl sulfate, tosylate, lactate, citrate, glycolate, glutamate and mixtures thereof. It is recognized that the cationic surfactant can be made in situ via the protonation of an amine. Additionally, the alkyl groups can also contain ether linkages or hydroxy or amino group substituents (e.g., the alkyl groups can contain polyethylene glycol and polyproylene glycol moieties). Preferred examples of cationic surfactants include distearyl dimethyl ammonium chloride and/or dipalmityl dimethyl ammonium chloride.

Other suitable cationic surfactants include protonated amines. The cationic protonated amines can be primary, secondary, or tertiary amines (preferably secondary or tertiary), depending upon the particular species and the selected pH of the present composition. Non-limiting examples of cationic protonated amines include stearamidopropyl dimethylamine, cocamidopropyl dimethylamine, lauramidopropyl dimethylamine, oleamidopropyl dimethylamine, palmitamidopropyl dimethylamine, and mixtures thereof.

Nonionic Surfactants

Nonionic surfactants can be optionally, and preferably, incorporated in the present compositions to enhance the rinseability of the present compositions from the skin. Nonionic surfactants, when present, are typically incorporated in the present compositions at a level of from about 0.01% to about 4%, preferably from about 0.1% to about 3%, and more preferably from about 0.2% to about 2%, by weight of the composition.

Among the nonionic surfactants that are useful herein are those that can be broadly defined as condensation products of long chain alcohols, e.g. $C_{8-30}$ alcohols, with sugar or starch polymers, i.e., glycosides. These compounds can be represented by the formula $(S)_n$—O—R wherein S is a sugar moiety such as glucose, sucrose, fructose, mannose, or galactose, n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_{8-20}$ alkyl group, and n is an integer of from about 1 to about 9. Commercially available examples of these surfactants include decyl polyglucoside and lauryl polyglucoside commercially-available from Cognis.

Other useful nonionic surfactants included the condensation products of sorbitol with a fatty acid. Non-limiting examples include the Tweens, Spans, and the Polysorbates.

Other useful nonionic surfactants include the condensation products of alkylene oxides with fatty acids (i.e. alkylene oxide esters of fatty acids). These materials have the general formula $RCO(X)_nOH$ wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100. Non-limiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants. A preferred polyhydroxy fatty acid amide surfactant is coconut alkyl N-methyl glucoside amide. Processes for making compositions containing polyhydroxy fatty acid amides are disclosed, for example, in G. B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934.

Non-limiting examples of suitable nonionic surfactants include: polyethylene glycol 20 sorbitan monolaurate (Polysorbate 20), polyethylene glycol 5 soya sterol, steareth-20, steareth-21, ceteareth-20, ceteareth-12, PPG-2 methyl glucose ether distearate, ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, diethanolamine cetyl phosphate, glyceryl stearate, PEG-100 stearate, and mixtures thereof. Preferred nonionic surfactants are those selected from the group consisting of steareth-21, ceteareth-20, ceteareth-12, Tween-60, Tween-80, sucrose cocoate, steareth-100, PEG-100 stearate, PEG-1000 stearate, and mixtures thereof.

Nonionic surfactants can be useful in facilitating the rinse properties of a composition comprising a gel network. Preferred nonionic surfactants will typically have an average HLB value of at least about 8, preferably at least about 9, more preferably at least about 10, more preferably at least about 11, and more preferably at least about 12. Additionally, preferred nonionic surfactants will have an average HLB value of no greater than about 20, preferably no greater than about 18, more preferably no greater than about 16, and more preferably no greater than about 14.

Additionally, preferred nonionic surfactants for facilitating rinse properties of the present compositions, especially those comprising a gel network, have alkyl chain lengths of from $C_8$ to $C_{16}$, preferably from $C_{10}$ to $C_{14}$, and more preferably from $C_{10}$ to $C_{12}$. Non-limiting examples of such nonionic surfactants include $C_8$-$C_{14}$ glucose amides, $C_8$-$C_{14}$ alkyl polyglucosides, $C_8$-$C_{14}$ alkyl glucosides, and $C_8$-$C_{14}$ alkyl ethoxylates.

Amphoteric Surfactants

The compositions of the present invention can optionally comprise from about 0.1% to about 20%, more preferably from about 0.2% to about 10%, and most preferably from about 0.5% to about 5%, by weight of the composition, of an amphoteric surfactant.

The term "amphoteric surfactant," as used herein, is also intended to encompass zwitterionic surfactants, which are a subset of amphoteric surfactants.

A wide variety of amphoteric surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, North American Edition (1992).

Nonlimiting examples zwitterionic surfactants are those selected from the group consisting of betaines, sultaines, hydroxysultaines, alkyliminoacetates, iminodialkanoates, aminoalkanoates, and mixtures thereof.

Preferred amphoteric surfactants include disodium lauroamphodiacetate, sodium lauroamphoacetate, cetyl dimethyl betaine (i.e. cetyl betaine), cocoamidopropyl betaine, cocoamidopropyl hydroxy sultaine, or mixtures thereof. Of these, cetyl dimethyl betaine (i.e. cetyl betaine) is especially preferred.

Anionic Surfactants

The compositions of the present invention can optionally comprise from about 0.1% to about 20%, more preferably from about 0.2% to about 10%, and most preferably from about 0.5% to about 5%, by weight of the composition, of an anionic surfactant.

Nonlimiting examples of anionic surfactants useful in the compositions of the present invention are disclosed in McCutcheon's, *Detergents and Emulsifiers*, North American edition (1986), published by allured Publishing Corporation; McCutcheon's, *Functional Materials*, North American Edition (1992); and U.S. Pat. No. 3,929,678, to Laughlin et al., issued Dec. 30, 1975 all of which are incorporated by reference herein in their entirety.

A wide variety of anionic surfactants are useful herein. Nonlimiting examples of anionic surfactants include the alkoyl isethionates, and the alkyl and alkyl ether sulfates. The alkoyl isethionates typically have the formula RCO—OCH$_2$CH$_2$SO$_3$M wherein R is alkyl or alkenyl of from about 10 to about 30 carbon atoms, and M is a water-soluble cation such as ammonium, sodium, potassium and triethanolamine Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae ROSO$_3$M and RO(C$_2$H$_4$O)$_x$SO$_3$M, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

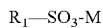

wherein R$_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials include the sarcosinates nonlimiting examples of which include sodium lauroyl sarcosinate, sodium cocoyl sarcosinate, and ammonium lauroyl sarcosinate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Other anionic materials include alkanoyl sarcosinates corresponding to the formula RCON(CH$_3$)CH$_2$CH$_2$CO$_2$M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Nonlimiting examples of preferred anionic surfactants useful herein include those selected from the group consisting of sodium lauryl sulfate, ammonium lauryl sulfate, ammonium cetyl sulfate, sodium cetyl sulfate, sodium stearyl sulfate, ammonium cocoyl isethionate, sodium lauroyl isethionate, sodium lauroyl sarcosinate, and mixtures thereof. A preferred anionic surfactant for use herein is sodium lauryl sulfate.

Humectants

A variety of humectants can be optionally employed in the present compositions at a level of from about 0.1% to about 20%, more preferably from about 0.5% to about 10%, and most preferably from about 1% to about 5%, by weight of the composition.

Nonlimiting examples of humectants include materials selected from the group consisting of guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, glycerol (i.e. glycerin), hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Also, useful are propoxylated glycerols as described in U.S. Pat. No. 4,976,953, to On et al., issued Dec. 11, 1990, which is incorporated by reference herein in its entirety.

A preferred humectant for use herein is glycerol (i.e. glycerin).

Exfoliating Agents

The present compositions can optionally further comprise exfoliating agents derived from a wide variety of particulate materials including those derived from inorganic, organic, natural, and synthetic sources.

The particulate exfoliating agents of the present invention, when present, are typically utilized at a level of from about 0.1% to about 20%, preferably from about 0.25% to about 10%, and more preferably from about 0.5% to about 5%, by weight of the composition. Non-limiting examples of these materials include those selected from the group consisting of almond meal, alumina, aluminum oxide, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e. polytetrafluoroethylene), polyhalogenated olefins, pumice rice bran, rye flour, sericite, silica, silk, sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are particles made from mixed polymers (e.g., copolymers, terpolymers, etc.), among such are polyethylene/polypropylene copolymer, polyethylene/propylene/isobutylene copolymer, polyethylene/styrene copolymer, and mixtures thereof. Typically, the polymeric and mixed polymeric particles are treated via an oxidation process to destroy impurities and the like. The polymeric and mixed polymeric particles can also optionally be cross linked with a variety of common crosslinking agents, non-limiting examples including butadiene, divinyl benzene, methylenebisacrylamide, allyl ethers of sucrose, allyl ethers of pentaerythritol, and mixtures thereof. Other examples of useful particles include waxes and resins such as paraffins, carnuba wax, ozekerite wax, candellila wax, urea-formaldehyde resins, and the like. When such waxes and resins are used herein it is important that these materials are solids at ambient and skin temperatures.

Among the preferred water-insoluble, particulate materials useful as exfoliating agents herein are the synthetic polymeric particles. Synthetic polymeric particles useful in the present invention are selected from the group consisting of polybutylene, polyethylene, polyisobutylene, polymethylstyrene, polypropylene, polystyrene, polyurethane, oxidized derivatives thereof, nylon, teflon, and mixtures thereof. Non-limiting examples of suitable exfoliating agents include oxidized polyethylene beads commercially available as A-C Oxidized Polyethylene beads from Honeywell and ACCUSCRUB™ beads from Accutech, LLC.

Interference Pigments

The present compositions can optionally further comprise interference pigments. An interference pigment is a pigment with pearl gloss prepared by coating the surface of a particle substrate material with a thin film. The particle substrate material is generally platelet in shape. The thin film is a transparent or semitransparent material having a high refractive index. The high refractive index material shows a pearl gloss resulting from mutual interfering action between reflection and incident light from the platelet substrate/coating layer interface and reflection of incident light from the surface of the coating layer. The present compositions preferably comprise no more than about 20%, more preferably no more than about 10%, even more preferably no more than about 7%, and still more preferably no more than about 5%, by weight of the composition, of interference pigment, when present. The present compositions preferably comprise at least about 0.01%, more preferably at least about 0.05%, even more preferably at least about 0.1%, and still more preferably at least about 0.2%, by weight of the composition, of interference pigment, when present.

In one embodiment, the interference pigment surface is either hydrophobic or has been hydrophobically modified. The greater the contact angle, the greater the hydrophobicity of the interference pigment. The interference pigments preferably possess a contact angle of at least about 60 degrees, more at least about 80 degrees, even more preferably at least about 100 degrees, and still more preferably at least about 110 degrees. The contact angle of the interference pigment can be determined according to the Particle Contact Angle Test described in U.S. Provisional Application Ser. No. 60/658,687, filed Mar. 4, 2005. The hydrophobically modified interference pigment ("HMIP") allows for the entrapment of the HMIP within the dispersed oil phase and greater deposition of the HMIP. In a preferred embodiment, the compositions contain both HMIPs and a dispersed oil phase. Preferably the weight ratio of HMIP to dispersed oil phase is from about 1:1 to about 1:70, more preferably from about 1:2 to about 1:50, still more preferably from about 1:3 to about 1:40 and most preferably from about 1:7 to about 1:35.

When formulated into a product, the HMIP's are preferably entrapped within the dispersed oil phase. This necessitates that the oil phase particle size is generally larger than the HMIP. In a preferred embodiment of the invention, the oil phase particles contain only a small number of HMIPs per oil particles. Preferably this is less than 20, more preferably less than 10, most preferably less than 5. These parameters, the relative size of the oil droplets to the HMIP and the approximate number of HMIP particles per dispersed oil particles, can be determined by using visual inspection with light microscopy.

The HMIP and the oil can be mixed into the composition via a premix or separately. For the case of separate addition, the hydrophobic pigments partition into the oil phase during the processing of the formulation. The HMIP of the present invention preferably has a hydrophobic coating comprising no more than about 20 weight percent of the total particle weight, more preferably no more than about 15 weight percent, even more preferably no more than about 10 weight percent. The HMIP of the present invention preferably has a hydrophobic coating comprising at least about 0.1 weight percent of the total particle weight, more preferably at least about 0.5 weight percent, even more preferably at least about 1 weight percent. Nonlimiting examples of the hydrophobic surface treatment useful herein include silicones, acrylate silicone copolymers, acrylate polymers, alkyl silane, isopropyl titanium triisostearate, sodium stearate, magnesium myristate, perfluoroalcohol phosphate, perfluoropolymethyl isopropyl ether, lecithin, carnauba wax, polyethylene, chitosan, lauroyl lysine, plant lipid extracts and mixtures thereof, preferably, silicones, silanes and stearates. Surface treatment suppliers include U.S. Cosmetics, KOBO Products Inc., and Cardre Inc.

The interference pigments of the present compositions are platelet particulates. The platelet particulates of the present compositions preferably have a thickness of no more than about 5 µm, more preferably no more than about 2 µm, still more preferably no more than about 1 µm. The platelet particulates of the present composition preferably have a thickness of at least about 0.02 µm, more preferably at least about 0.05 µm, even more preferably at least about 0.1 µm, and still more preferably at least about 0.2 µm.

The particle size typically determines the opacity and luster. The particle size is determined by measuring the diameter thickness of the particulate material. The term "diameter" as used herein, means the largest distance across the major axis of the particulate material. Diameter can be determined by any suitable method known in the art, such as particle size analyzer Mastersizer 2000 manufactured by Malvern Instruments. The interference pigment of the present compositions preferably have an average diameter not greater than about 200 µm, more preferably not greater than 100 µm, even more preferably not greater than about 80 µm, still more preferably not greater than about 60 µm. The interference pigment of the present compositions preferably have a diameter of at least about 0.1 µm, more preferably at least about 1.0 µm, even more preferably at least about 2.0 µm, and still more preferably at least about 5.0 µm.

The interference pigment of the present compositions comprises a multilayer structure. The centre of the particulates is a flat substrate with a refractive index (RI) normally below 1.8. A wide variety of particle substrates are useful herein. Nonlimiting examples are natural mica, synthetic mica, graphite, talc, kaolin, alumina flake, bismuth oxychloride, silica flake, glass flake, ceramics, titanium dioxide, $CaSO_4$, $CaCO_3$, $BaSO_4$, borosilicate and mixtures thereof, preferably mica, silica and alumina flakes.

A layer of thin film or a multiple layer of thin films are coated on the surface of a substrate described above. The thin films are made of highly refractive materials. The refractive index of these materials is normally above 1.8.

A wide variety of thin films are useful herein. Nonlimiting examples are $TiO_2$, $Fe_2O_3$, $SnO_2$, $Cr_2O_3$, ZnO, ZnS, ZnO, SnO, $ZrO_2$, $CaF_2$, $Al_2O_3$, BiOCl, and mixtures thereof or in the form of separate layers, preferably $TiO_2$, $Fe_2O_3$, $Cr_2O_3SnO_2$. For the multiple layer structures, the thin films can be consisted of all high refractive index materials or alternation of thin films with high and low RI materials with the high RI film as the top layer.

The interference color is a function of the thickness of thin film, the thickness for a specific color may be different for different materials. For $TiO_2$, a layer of 40 nm to 60 nm or a whole number multiple thereof gives silver color, 60 nm to 80 nm yellow color, 80 nm to 100 nm red color, 100 nm to 130 nm blue color, 130 nm to 160 nm green color. In addition to the interference color, other transparent absorption pigments can be precipitated on top of or simultaneously with the $TiO_2$ layer. Common materials are red or black iron oxide, ferric ferrocyanide, chromium oxide or carmine. The color of the interference pigment in addition to its brightness can have a significant influence on human perception of skin tone. In general, preferred colors are silver, gold, red, green, or mixtures thereof.

Non-limiting examples of the interference pigments useful herein include those supplied by Persperse, Inc. under the trade name PRESTIGE®, FLONAC®; supplied by EMD Chemicals, Inc. under the trade name TIMIRON®, COLORONA®, DICHRONA® and XIRONA®; and supplied by Engelhard Co. under the trade name FLAMENCO®, TIMICA®, DUOCHROME®.

Polymeric Thickeners

The compositions of the present invention, in some embodiments, may further include one or more polymeric thickeners. When present, polymeric thickeners are typically incorporated in the present compositions at a level of no more than about 10%, preferably no more than about 8%, and still more preferably no more than about 7%, by weight of the composition. When present, the polymeric thickeners are preferably incorporated in the present compositions at a level of at least about 0.01%, more preferably at least about 0.05%, and still more preferably at least about 0.1%, by weight of the composition. It can often be useful to blend different polymeric thickeners together to generate an optimal stability and rheology profile.

Non-limiting examples of polymeric thickeners useful herein include carboxylic acid polymers such as the carbomers (such as those commercially available under the tradename CARBOPOL® 900 series from B.F. Goodrich; e.g., CARBOPOL® 954) and the Luvigel series from BASF. Other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerythritol. These copolymers are known as acrylates/$C_{10-30}$ alkyl acrylate crosspolymers and are commercially available as CARBOPOL® 1342, CARBOPOL® 1382, CARBOPOL® Ultrez 21, CARBOPOL® Ultrez 20, CARBOPOL® Ultrez 10, PEMULEN® TR-1, and PEMULEN® TR-2, from B.F. Goodrich.

Other non-limiting examples of polymeric thickeners include crosslinked polyacrylate polymers including both cationic and nonionic polymers.

Still other non-limiting examples of polymeric thickeners include the polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Tradename SEPIGEL® 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include HYPAN® SR150H, SS500V, SS500W, SSSA100H, from Lipo Chemicals, Inc., (Patterson, N.J.).

Another non-limiting class of polymeric thickeners useful herein are the polysaccharides. Non-limiting examples of polysaccharide gelling agents include those selected from cellulose, and cellulose derivatives. Preferred among the alkyl hydroxyalkyl cellulose ethers is the material given the CTFA designation cetyl hydroxyethylcellulose, which is the ether of cetyl alcohol and hydroxyethylcellulose, sold under the tradename NATROSEL® CS PLUS from Aqualon Corporation (Wilmington, Del.). Other useful polysaccharides include scleroglucans which are a linear chain of (1-3) linked glucose units with a (1-6) linked glucose every three units, a commercially available example of which is CLEAROGEL™ CS 11 from Michel Mercier Products Inc. (Mountainside, N.J.).

Another non-limiting class of polymeric thickeners useful herein are the gums. Non-limiting examples of gums useful herein include hectorite, hydrated silica, xantham gum, and mixtures thereof.

Yet another non-limiting class of polymeric thickeners useful herein are the modified starches. Acrylate modified starches such as WATERLOCK® from Grain Processing Corporation may be used. Hydroxypropyl starch phosphate, tradename STRUCTURE XL® from National Starch is another example of a useful modified starch, and other useful examples include ARISTOFLEX® HMB (Ammonium Acrylodimethyltaruate/Beheneth-25 Methacrylate Crosspolymer) from Clariant and cationic stabylens.

Silicones

Silicones such as polydialkylsiloxanes, polydiarylsiloxanes, polyalkarylsiloxanes, and cylcomethicones having 3 to 9 silicon atoms can be useful optional ingredients in the present compositions. These silicones include both volatile and nonvolatile materials. These silicones are disclosed in U.S. Pat. No. 5,069,897, to Orr, issued Dec. 3, 1991, which is incorporated by reference herein in its entirety. The polyalkylsiloxanes include, for example, polyalkylsiloxanes with viscosities of from about 0.5 to about 600,000 centistokes at 25° C. Such polyalkylsiloxanes correspond to the general chemical formula $R_3SiO[R_2SiO]_xSiR_3$ wherein R is an alkyl group (preferably R is methyl or ethyl, more preferably methyl) and x is an integer chosen to achieve the desired viscosity. Commercially available polyalkylsiloxanes include the polydimethylsiloxanes, which are also known as dimethicones, nonlimiting examples of which include the VICASIL series sold by General Electric Company and the Dow Corning® 200 series sold by Dow Corning Corporation. Cyclic polyalkylsiloxanes useful herein include those corresponding to the general chemical formula $[SiR_2—O]_n$ wherein R is an alkyl group (preferably R is methyl or ethyl, more preferably methyl) and n is an integer from about 3 to about 9, more preferably n is an integer from about 3 to about 7, and most preferably n is an integer from about 5 to about 6. When R is methyl, these materials are typically referred to as cyclomethicones. Also useful are materials such as trimethylsiloxysilicate, which is a polymeric material corresponding to the general chemical formula $[(CH_2)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl). Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation). The silicones described herein can be blended with silicone gums to deliver desirable sensory and skin conditioning benefits. Such blends are commercially available from Dow Corning and GE Silicones. In addition, emulsified silicone gums are commercially available and suitable for use in the present compositions.

When present, the present compositions typically comprise from about 0.1% to about 25%, preferably from about 0.5% to about 20%, and more preferably from about 1% to about 10%, by weight of the composition, of silicone.

Silicone Elastomers

The compositions of the present invention can optionally further comprise from about 0.1% to about 30%, by weight of the composition, of a silicone elastomer component. Preferred levels of silicone elastomer are from about 0.5% to about 30%, and more preferably from about 1% to about 20%, by weight of the composition.

Suitable for use herein are silicone elastomers which can be emulsifying or non-emulsifying crosslinked siloxane elastomers or mixtures thereof. No specific restriction exists as to the type of curable organopolysiloxane composition that can serve as starting material for the crosslinked organopolysiloxane elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane and condensation-curing organopolysiloxane compositions which cure in the presence of an organotin compound or a titanate ester.

Addition reaction-curing organopolysiloxane compositions can be preferred for their rapid curing rates and excellent uniformity of curing. A preferred addition reaction-curing organopolysiloxane composition is prepared from:

(A) an organopolysiloxane having at least 2 lower alkenyl groups in each molecule;

(B) an organopolysiloxane having at least 2 silicon-bonded hydrogen atoms in each molecule; and (C) a platinum-type catalyst.

The compositions of the present invention can optionally include an emulsifying crosslinked organopolysiloxane elastomer, a non-emulsifying crosslinked organopolysiloxane elastomer, or a mixture thereof. The term "non-emulsifying," as used herein, defines crosslinked organopolysiloxane elastomers from which polyoxyalkylene units are absent. The term "emulsifying," as used herein, means crosslinked organopolysiloxane elastomers having at least one polyoxyalkylene (e.g., polyoxyethylene or polyoxypropylene) unit. Preferred emulsifying elastomers herein include polyoxyalkylene modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin. Emulsifying crosslinked organopolysiloxane elastomers can notably be chosen from the crosslinked polymers described in U.S. Pat. No. 5,412,004, U.S. Pat. No. 5,837,793, and U.S. Pat. No. 5,811,487. In addition, an emulsifying elastomer comprised of dimethicone copolyol crosspolymer (and) dimethicone is available from Shin Etsu under the tradename KSG-21.

Advantageously, the non-emulsifying elastomers are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), and Grant Industries (GRANSIL™ line of elastomers). Cross-linked organopolysiloxane elastomers useful in the present invention and processes for making them are further described in U.S. Pat. No. 4,970,252, U.S. Pat. No. 5,760,116, and U.S. Pat. No. 5,654,362. Additional crosslinked organopolysiloxane elastomers useful in the present invention are disclosed in Japanese Patent Application JP 61-18708, assigned to Pola Kasei Kogyo KK.

Commercially-available silicone elastomers preferred for use herein are Dow Corning's 9040 silicone elastomer blend, Shin Etsu's KSG-21, and mixtures thereof.

Aqueous Carrier

The present compositions preferably comprise water. The present compositions will typically comprise at least about 20%, preferably at least about 30%, more preferably at least about 40%, and more preferably at least about 50%, by weight of the composition, of water.

The present compositions can further comprise optional solvents such as ethanol, isopropanol, and mixtures thereof. In one embodiment, the present compositions comprise less than about 50%, preferably less than about 30%, and more preferably less than about 10%, by weight of the composition, of alcohol solvent, such as those selected from the group consisting of ethanol, isopropanol, and mixtures thereof. In one embodiment, the present compositions comprise less than about 1%, preferably 0%, by weight of the composition, of alcohol solvent, such as those selected from the group consisting of ethanol, isopropanol, and mixtures thereof.

Other Optional Ingredients

The present compositions can further comprise additional optional ingredients. Suitable additional optional ingredients include perfume, preservatives, chelants, sensates, desquamation actives, anti-acne actives, anti-wrinkle/anti-atrophy actives, anti-oxidants/radical scavengers, flavonoids, anti-inflammatory agents, anti-cellulite agents, topical anesthetics, tanning actives, skin lightening agents, skin soothing and healing actives, antimicrobial actives, sunscreen actives, visual skin enhancers, and the like. Such optional ingredients are described more fully in U.S. Provisional Application Ser. No. 60/658,687, filed Mar. 4, 2005.

In one embodiment, the present compositions are substantially free, or free, of active ingredients such as those disclosed in U.S. Pat. No. 5,811,111, at column 8, line 10 to column 10, line 16.

In one embodiment, the present compositions are substantially free, or free, of salicylic acid.

The compositions of the present invention will typically have a pH in the range of from about 3 to about 9, preferably from about 4 to about 8, and more preferably from about 5 to about 7.

Packaging

The compositions of the present invention can be packaged in a variety of suitable containers. Non-limiting examples of suitable containers include tubes, bottles, tottles, hand pump containers, and the like. The container is typically made of a plastic material. Examples of suitable plastic materials include high density polyethylene ("HDPE"), low density polyethylene ("LDPE"), polyethylene terephthalate ("PET"), polypropylene ("PP"), polyvinyl chloride, polycarbonate, nylon, and fluorinated ethylene propylene. The bottle can be made via a number of various processes known in the art, such as blow molding, injection molding, and the like. Preferred bottles of the present invention are made of HDPE or PP via an extrusion blow molding process, or PET via an injection blow molding process.

Methods of Cleansing Skin

The present invention also relates to methods of cleansing the skin, wherein the method comprises contacting the skin with a composition of the present invention and rinsing the skin with water or wiping the skin with a substrate, to remove at least a portion of the composition from the skin.

In preferred embodiments, the compositions of the present invention are also useful for cleansing and/or hydrating skin, especially for cleansing of the face and neck areas. Typically, a suitable or effective amount of the cleansing composition is applied to the area to be cleansed and/or hydrated. Alternatively, a suitable amount of the cleansing composition can be applied via intermediate application to a washcloth, sponge, pad, cotton ball or other application device. If desired, the area to be cleansed can be premoistened with water. It has been found that the compositions of the present invention can be combined with water during the cleansing process and rinsed-off from the skin. Alternatively, the composition can be used alone and wiped-off from the skin using a pad, cotton ball, tissue, or other like device or substrate. The cleansing process is typically a two-step process involving application of the composition followed either by rinsing of the product with water or wiping without the use of water. Generally, an effective amount of composition to be used will depend upon the needs and usage habits of the individual.

Lipid Modulus Test Method

Lipid rheology is first measured on a TA Instruments AR2000 stress-controlled rheometer with a Peltier temperature controlled sample stage or an equivalent. A parallel plate geometry is used with a 40 mm plate and a 1 mm gap. The lower plate is heated to 85° C. and the melted lipid and structurant (if present) is added onto the lower plate and allowed to equilibrate. The upper plate is then lowered to the 1 mm gap while ensuring the lipid fills the gap fully, spinning the top plate and adding more lipid to promote wicking, and the sample is cooled quickly to 25° C. and equilibrated at 25° C. for 5 minutes. Viscosity is then measured using a stress-ramp procedure common on these types of machines using a logarithmic stress ramp from 20 to 2500 Pa for a 2-minute duration, with 60 measurements points per decade. The starting and ending stress is sufficient to induce flow and reach a shear rate of at least 10 sec-1. Viscosity is recorded and the data fitted to a power law model using Equation 1. Only points between 0.001 sec-1 and 40 seconds-1 are to be used in the power law fit. The viscosity at 1.0 sec-1 is calculated from Equation 1. One should carefully watch the sample during the test so that when the material is ejected from under the plate, the method is stopped.

$$\eta = \kappa \cdot \gamma(dot)^{(n-1)} \qquad \text{Equation 1:}$$

Where $\eta$=viscosity, $\kappa$ is the consistency and $\gamma$ (dot) is the shear rate and n is the shear index.

The Lipid Modulus Test utilizes the data collected from the Lipid Rheology Test. In this case, the data is plotted as stress (Pa) vs. % Strain. The Modulus is obtained by recording the value at 200% strain (using visual extrapolation if there is not a data point at 200% strain) and dividing this value by 2 (200% strain is a strain of 2) to obtain the lipid modulus. In general, five samples are run and the high and low values are discarded and the middle three values are averaged to obtain a Lipid Modulus Value.

EXAMPLES

The following are non-limiting examples of compositions of the present invention. The compositions are in the form of cleansing creams or cleansing milks and are suitable for cleansing skin.

| Ingredients | EX 1 | EX 2 | EX 3 | EX 4 | EX 5 | EX 6 |
|---|---|---|---|---|---|---|
| Mix A | | | | | | |
| Water | QS 100 | QS 100 | QS 100 | QS 100 | QS 100 | QS 100 |
| Glycerin | 3 | 5 | 5 | 3 | 3 | 3 |
| Decyl Glucoside[1] | — | — | 1.25 | 2.5 | 2.5 | 2.5 |
| Disodium EDTA | 0.01 | 0.01 | 0.01 | 0.01 | 0.01 | 0.01 |
| Mix B | | | | | | |
| Isopropyl Palmitate[2] | 15 | 10 | 15 | 15 | 10 | 8 |
| Mineral Oil[3] | 1.75 | 1.0 | 1.75 | 1.75 | — | — |
| Petrolatum | 3.25 | 2.0 | 3.25 | 3.25 | 6 | 5 |
| Behenyl Alcohol | — | 0.25 | — | 0.25 | 0.25 | — |
| Stearyl Alcohol | 1.33 | 0.75 | 1.5 | .75 | 0.75 | 1.33 |
| Cetyl Alcohol | 1.33 | 2.50 | 1.5 | 2.5 | 2.5 | 1.33 |
| Distearyl Dimethyl Ammonium Chloride[4] | 1.0 | 1.5 | 1.25 | 1.5 | 1.5 | 1.5 |
| Steareth-21[5] | 0.5 | 0.5 | 0.5 | 0.5 | 0.5 | 0.5 |
| Steareth-2[6] | 0.25 | 0.25 | 0.25 | 0.25 | 0.25 | 0.25 |
| Mix C | | | | | | |
| Oxidized Polyethylene Beads[7] | — | 1.0 | — | 1.0 | 1.0 | — |
| Fragrance | 0.2 | 0.15 | 0.15 | 0.15 | 0.15 | 0.15 |
| Menthol | — | 0.05 | — | — | — | — |
| Mix D | | | | | | |
| Cetyl Betaine[8] | 2 | 2 | 2 | 2 | 2 | 2 |
| Sodium Lauryl Sulfate[9] | 1 | 1 | 1 | 1 | 1 | 1 |
| Glydant Plus | 0.3 | 0.3 | 0.3 | 0.3 | 0.3 | 0.3 |
| Mix E | | | | | | |
| Cyclomethicone D5 | — | — | — | — | 5 | — |
| DC 9040 Silicone Elastomer[10] | — | — | — | — | 5 | — |
| Dimethicone (30,000 cts) | — | — | — | — | — | 3 |

[1] Available as Plantaren 2000USP (Cognis Corp)
[2] Available as Stepan IPP (Stepan)
[3] Available as Hydrobright 1000 (Crompton)
[4] Available as Arosurf TA-100 (Degussa)
[5] Available as Brij 721 (Uniqema)
[6] Available as Brij 72 (Uniqema)
[7] Available as A-C Oxidized Polyethylene (Honeywell)
[8] Available as Lonzaine SP16 (Lonza)
[9] Available as Stepanal WAC (Stepan)
[10] Available as a silicone elastomer dispersion from Dow Corning Corp.

The compositions of Examples 1-6 can be made as follows. In a suitable vessel, heat the Mix A ingredients with stirring to about 75° C. In a separate vessel, heat the Mix B ingredients with stirring to about 75° C. Add Mix B to Mix A with mixing. Add Mix C to Mixes A & B. Cool the mixture to about 50° C. and add Mix E with proper mixing to ensure emulsification. Cool mixture to about 35° C. In a separate vessel, combine the Mix D ingredients and add to the remaining mixture with stirring.

| Ingredients | EX 7 | EX 8 | EX 9 | EX 10 | EX 11 | EX 12 |
|---|---|---|---|---|---|---|
| Mix A | | | | | | |
| Carbomer[11] | 0.15 | 0.16 | 0.16 | 0.14 | 0.2 | 0.2 |
| Water | 19.85 | 19.8 | 19.85 | 19.86 | 19.85 | 19.85 |
| Mix B | | | | | | |
| Pemulen TR1 | 0.1 | 0.12 | 0.11 | 0.1 | 0.15 | 0.15 |
| Water | 14.9 | 14.85 | 14.9 | 14.9 | 14.9 | 14.9 |
| Mix C | | | | | | |
| Sodium Hydroxide | 0.065 | 0.065 | 0.65 | 0.65 | 0.07 | 0.07 |
| Water | 2.217 | 2.217 | 2.217 | 2.217 | 2.217 | 2.217 |
| Mix D | | | | | | |
| Water | QS 100 | QS 100 | QS 100 | QS 100 | QS 100 | QS 100 |
| Disodium EDTA | 0.1 | 0.1 | 0.1 | 0.1 | 0.1 | 0.1 |
| Glycerin | 4 | 4 | 6 | 4 | 4 | 4 |
| Mix E | | | | | | |
| Isopropyl Palmitate[12] | 10 | 7.5 | 10 | 15 | 15 | 15 |
| Mineral Oil[13] | 1.75 | 0.875 | 1.75 | 1.75 | — | — |
| Petrolatum | 3.25 | 1.625 | 3.25 | 3.25 | 7 | 7 |
| Stearyl alcohol | 0.875 | 0.875 | 0.875 | 0.875 | 1 | 1 |
| Cetyl alcohol | 0.875 | 0.875 | 0.875 | 0.875 | 1 | 1 |
| Stearic Acid | 0.11 | 0.11 | 0.11 | 0.11 | 0.2 | 0.2 |
| Steareth-21[14] | 0.5 | 0.5 | 0.5 | 0.5 | 0.7 | 0.7 |
| Steareth-2[15] | 0.25 | 0.25 | 0.25 | 0.25 | 0.4 | 0.4 |
| Methylparaben | 0.2 | 0.2 | 0.2 | 0.2 | — | — |
| Propylparaben | 0.15 | 0.15 | 0.15 | 0.15 | — | — |
| Dimethicone (30,000 cts) | — | — | — | — | — | 2 |
| DMDM Hydantoin/ Iodopropynyl Butyl-carbamate[16] | — | — | — | — | 0.3 | 0.3 |
| Decyl Glucosides[17] | 0.48 | 0.48 | 0.48 | 0.48 | — | — |
| Fragrance | 0.15 | 0.15 | 0.15 | 0.15 | 0.25 | 0.25 |

[11] Available as Carbopol 954 (BF Goodrich).
[12] Available as Stepan IPP (Stepan).
[13] Available as Hydrobright 1000 (Crompton).
[14] Available as Brij 721 (Uniqema).
[15] Available as Brij 72 (Uniqema).
[16] Available as Glydant Plus (Lonza).
[17] Available as Plantaren 2000USP (Cognis Corp).

The compositions of Examples 7-12 can be made as follows. Agitate Mixes A, B, & C until they are dispersed into the water. After polymers and sodium hydroxide are dispersed in water add Mixes A, B, & C into Mix D in a suitable container. While mixing with a propeller, heat this mixture to 70-75° C. Add oil phase ingredients together into a suitable container and while mixing with a propeller, heat this mixture to 75-80° C. Remove heat and add pre mixes to oil phase while mixing oil phase with a propeller until it is homogeneous. Continue mixing until temperature drops to 45-50° C., add fragrance, Glydant Plus and decyl glucoside and continue mixing with a propeller. While mixing with a propeller, cool the batch to 35-40° C., ensuring that the batch is smooth and homogeneous. Transfer the batch to containers for storage.

| Ingredients | EX 13 | EX 14 | EX 15 |
|---|---|---|---|
| Isopropyl palmitate[18] | 15 | 15 | 15 |
| Mineral Oil[19] | 1.75 | 1.75 | 1.75 |
| Petrolatum[20] | 3.25 | 3.25 | 3.25 |
| Behenyl trimethyl ammonium chloride[21] | 2.25 | — | 2.25 |
| Isopropyl alcohol | 0.598 | — | 0.598 |
| Stearamidopropyl dimethylamine[22] | — | 2 | — |
| L-Glutamic acid[23] | — | 0.64 | — |
| Cetyl alcohol[24] | 1.86 | 2 | 1.86 |
| Stearyl alcohol[25] | 4.64 | 4.5 | 4.64 |
| Benzyl alcohol[26] | 0.4 | 0.4 | 0.4 |

-continued

| Ingredients | EX 13 | EX 14 | EX 15 |
|---|---|---|---|
| Methylchloroisothiazolinone/ Methylisothiazolinone[27] | 0.0005 | 0.0005 | 0.0005 |
| Perfume | 0.5 | 0.25 | 0.5 |
| NaOH | 0.014 | — | 0.014 |
| Panthenol[28] | 0.05 | 0.05 | 0.05 |
| Panthenyl ethyl ether[29] | 0.05 | 0.05 | 0.05 |
| Disodium EDTA[30] | 0.127 | — | 0.127 |
| EDTA[31] | — | 0.1 | — |
| Polyoxyethylene (12) tridecyl ether[32] | — | — | 0.1 |
| Deionized Water | | QS to 100% | |

[18]Kessco IPP available from Stepan Chemicals.
[19]Hydrobrite 1000 PO available from Crompton Corporation.
[20]Super White Protopet available from Witco Chemicals.
[21]Genamin KDMP available from Clariant.
[22]Lexamine S-13 available from Inolex.
[23]Available from Ajinmoto.
[24]CO-1695F available from P&G Chemicals.
[25]CO-1897F available from P&G Chemicals.
[26]Available from Charkit Chemicals.
[27]Kathon CG available from Rohm & Haas.
[28]Available from Roche.
[29]Available from Roche.
[30]Dissolvine NA2-S available from Akzo Nobel.
[31]Dissolvine Z available from Akzo Nobel.
[32]Renex 30 available from Uniquema Americas.

The compositions of Examples 13-15 can be made as follows. Heat deionized water to 85° C. Mix cationic surfactants and high melting point fatty compounds into the water. Add the isopropyl palmitate, mineral oil, and petrolatum. Maintain the water at a temperature of about 85° C. until the components are homogenized and no solids are observed. Cool the mixture to about 55° C. and maintain at this temperature to form a gel matrix. Maintain the gel matrix at about 50° C. during this time with constant stirring to assure homogenization. When included, add other additional components such as perfumes, rheology modifiers, and preservatives at this point also. After homogenization, cool to room temperature.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

It should be understood that every maximum numerical limitation given throughout this specification will include every lower numerical limitation, as if such lower numerical limitations were all expressly written herein. Every minimum numerical limitation given throughout this specification will include every higher numerical limitation, as if such higher numerical limitations were all expressly written herein. Every numerical range given throughout this specification will include every narrower numerical range that falls within such broader numerical range, as if such narrower numerical ranges were all expressly written herein.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of cleansing skin, said method comprising the steps of:
  (a) contacting said skin with a composition comprising:
    i) from about 8% to about 20%, by weight of the cleansing composition, of a fatty ester selected from the group consisting of isopropyl palmitate, isopropyl isostearate, and a mixture thereof;
    ii) from about 1% to about 10%, by weight of the cleansing composition, of a high modulus lipid comprising petrolatum and mineral oil;
    iii) a surfactant combination comprising from about 0.2% to about 2%, by weight of the cleansing composition, of a nonionic surfactant; from about 0.5% to about 5%, by weight of the cleansing composition, of an anionic surfactant; and from about 0.5% to about 5%, by weight of the cleansing composition; of an amphoteric surfactant;
    iv) a humectant; and
    v) a hydrophobic structuring agent; and
  (b) rinsing said skin with water or wiping said skin with a substrate.

2. The method of claim 1, wherein said hydrophobic structuring agent is selected from the group consisting of cetyl alcohol, stearyl alcohol, behenyl alcohol, and mixtures thereof.

3. The method of claim 2, wherein the nonionic surfactant comprises decyl polyglucoside.

4. The method of claim 3, wherein the amphoteric surfactant comprises cetyl betaine.

5. The method of claim 4, wherein the anionic surfactant comprises sodium lauryl sulfate.

6. The method of claim 5, wherein the humectant comprises glycerin.

7. The method of claim 6, wherein said composition further comprises a cationic surfactant.

8. The method of claim 7, wherein said cationic surfactant is selected from the group consisting of distearyl dimethyl ammonium chloride, behenyl trimethyl ammonium chloride, stearamidopropyl dimethylamine, and mixtures thereof.

* * * * *